(12) United States Patent
Zampieri et al.

(10) Patent No.: US 11,160,806 B2
(45) Date of Patent: Nov. 2, 2021

(54) SALT OF N-(2,6-DIETHYLPHENYL)-8-({4-[4-(DIMETHYLAMINO)PIPERIDIN-1-YL]-2-METHOXYPHENYL}AMINO)-1-METHYL-4,5-DIHYDRO-1H-PYRAZOLO[4,3-H]QUINAZOLINE-3-CARBOXAMIDE, ITS PREPARATION, AND FORMULATIONS CONTAINING IT

(71) Applicant: LES LABORATOIRES SERVIER, Suresnes (FR)

(72) Inventors: Massimo Zampieri, Cesano Maderno (IT); Marina Caldarelli, Milan (IT); Ilaria Candiani, Busto Arsizio (IT); Matteo D'Anello, Novate Milanese (IT); Germano D'Arasmo, Arese (IT)

(73) Assignee: NERVIANO MEDICAL SCIENCES S.r.l., Nerviano (IT)

( * ) Notice: Subject to any disclaimer, the term of this patent is extended or adjusted under 35 U.S.C. 154(b) by 0 days.

(21) Appl. No.: 16/624,488

(22) PCT Filed: Jun. 28, 2018

(86) PCT No.: PCT/EP2018/067394
§ 371 (c)(1),
(2) Date: Dec. 19, 2019

(87) PCT Pub. No.: WO2019/002454
PCT Pub. Date: Jan. 3, 2019

(65) Prior Publication Data
US 2020/0246339 A1    Aug. 6, 2020

(30) Foreign Application Priority Data
Jun. 29, 2017    (EP) .................... 17305826

(51) Int. Cl.
*C07D 487/04*    (2006.01)
*A61K 31/519*    (2006.01)
*A61P 35/00*    (2006.01)

(52) U.S. Cl.
CPC ............ *A61K 31/519* (2013.01); *A61P 35/00* (2018.01); *C07D 487/04* (2013.01)

(58) Field of Classification Search
CPC ..................................... C07D 487/04
See application file for complete search history.

(56) References Cited

FOREIGN PATENT DOCUMENTS

| EP | 2303891 | 2/2016 |
|---|---|---|
| WO | WO2009/156315 | * 12/2009 |

OTHER PUBLICATIONS

International Search Report for PCT/EP2018/067394 dated Jul. 27, 2018.

* cited by examiner

Primary Examiner — Brian E McDowell
(74) Attorney, Agent, or Firm — Hueschen and Sage

(57) ABSTRACT

New N-(2,6-diethylphenyl)-8-({4-[4-(dimethyl amino)piperidin-1-yl]-2-methoxyphenyl}amino)-1-methyl-4,5-dihydro-1H-pyrazolo[4,3-h]quinazoline-3-carboxamide phosphate of formula (II):

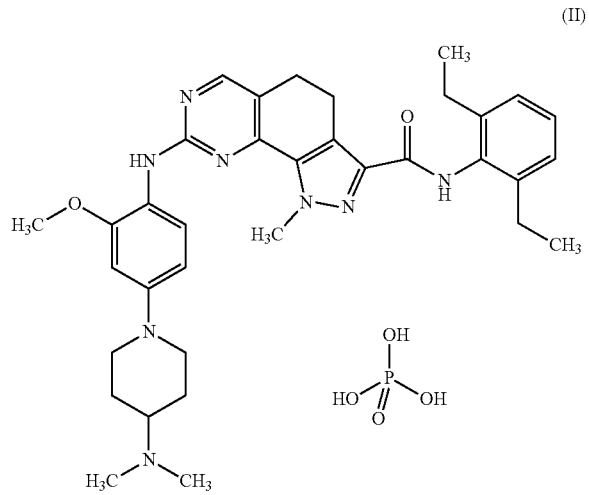

Medicaments.

6 Claims, 5 Drawing Sheets

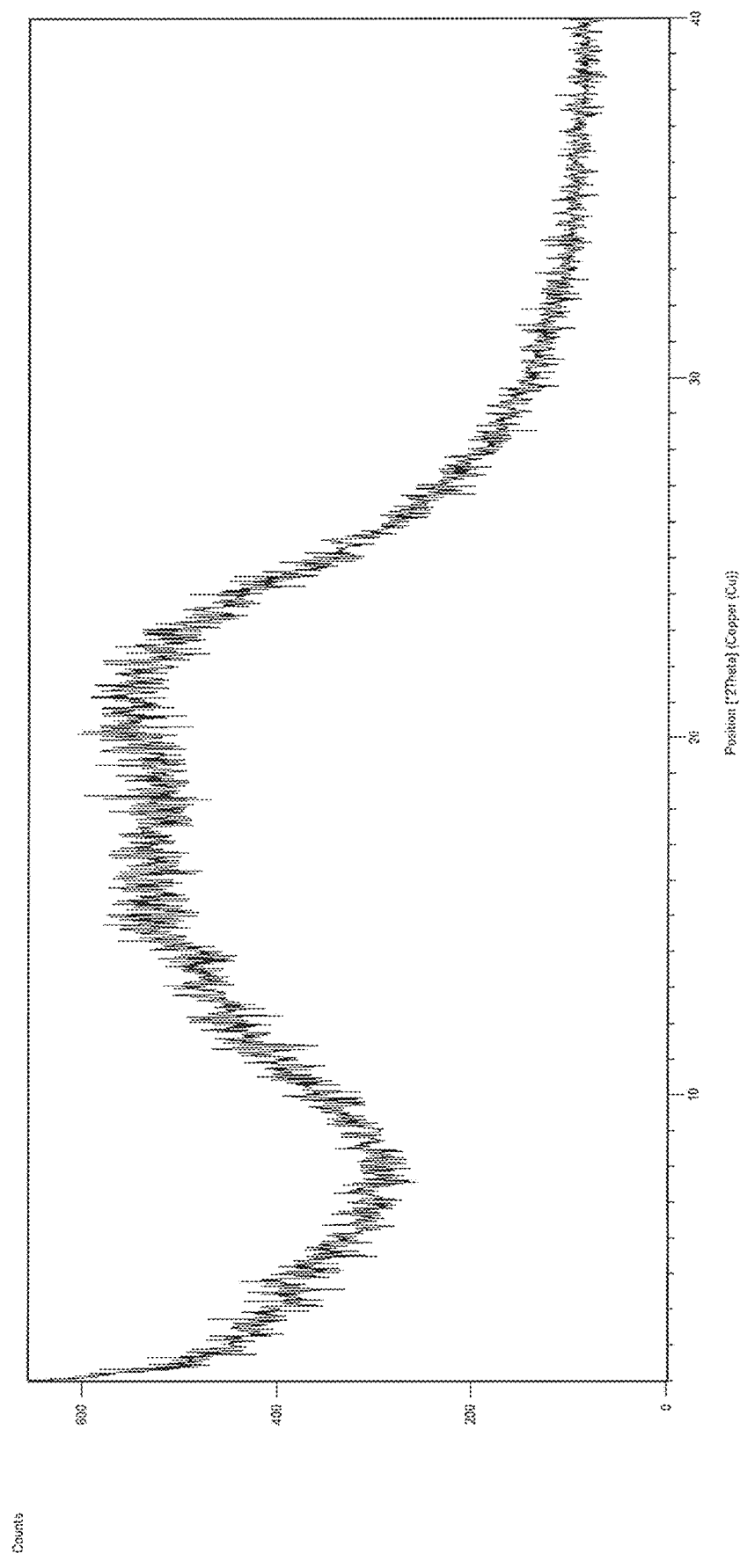
Figure 1: X-ray diffraction diagram of amorphous form of N-(2,6-diethylphenyl)-8-({4-[4-(dimethylamino)piperidin-1-yl]-2-methoxyphenyl}amino)-1-methyl-4,5-dihydro-1H-pyrazolo[4,3-h]quinazoline-3-carboxamide (free base)

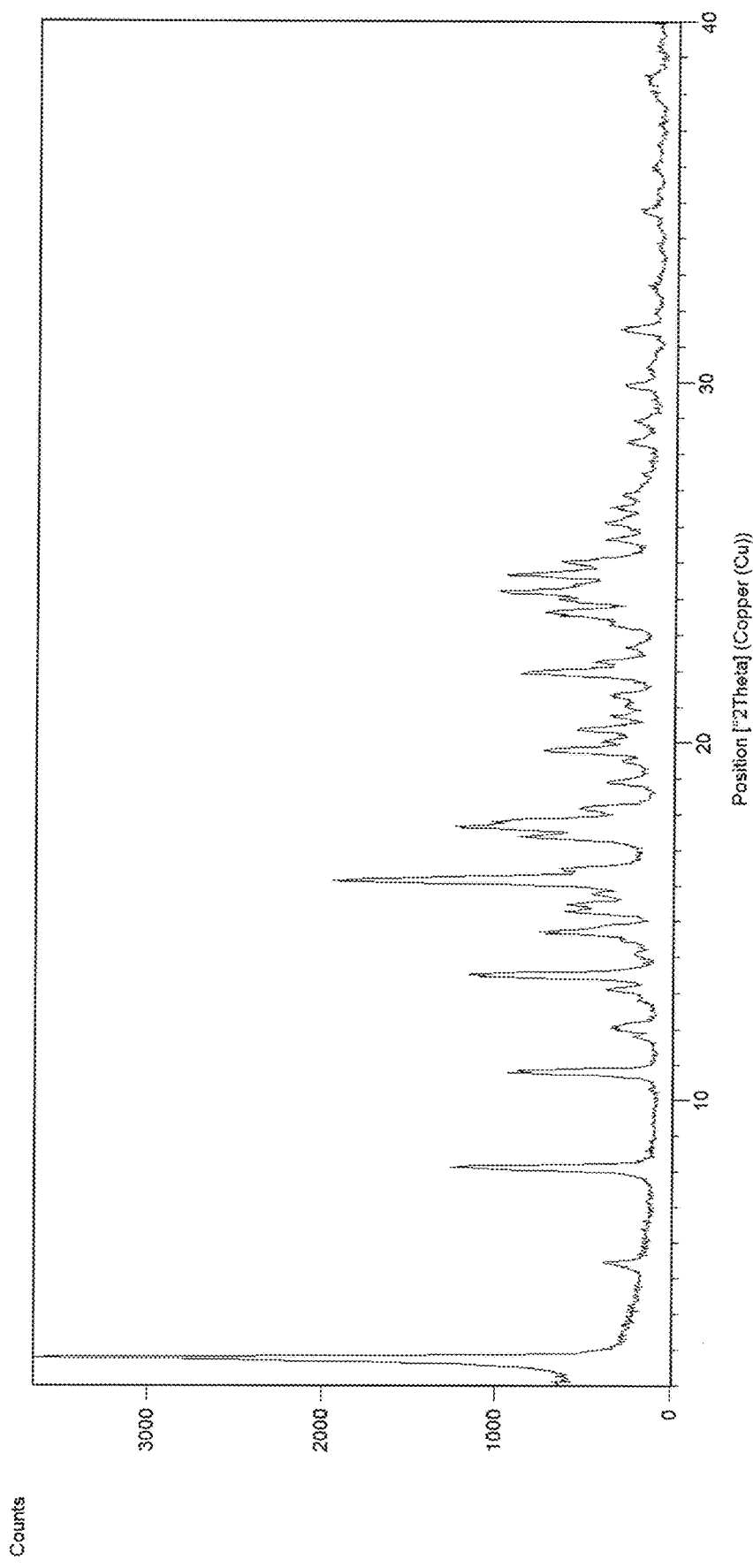
Figure 2: X-ray powder diffraction diagram of N-(2,6-diethylphenyl)-8-({4-[4-(dimethylamino)piperidin-1-yl]-2-methoxyphenyl}amino)-1-methyl-4,5-dihydro-1H-pyrazolo[4,3-h]quinazoline-3-carboxamide phosphate Form I

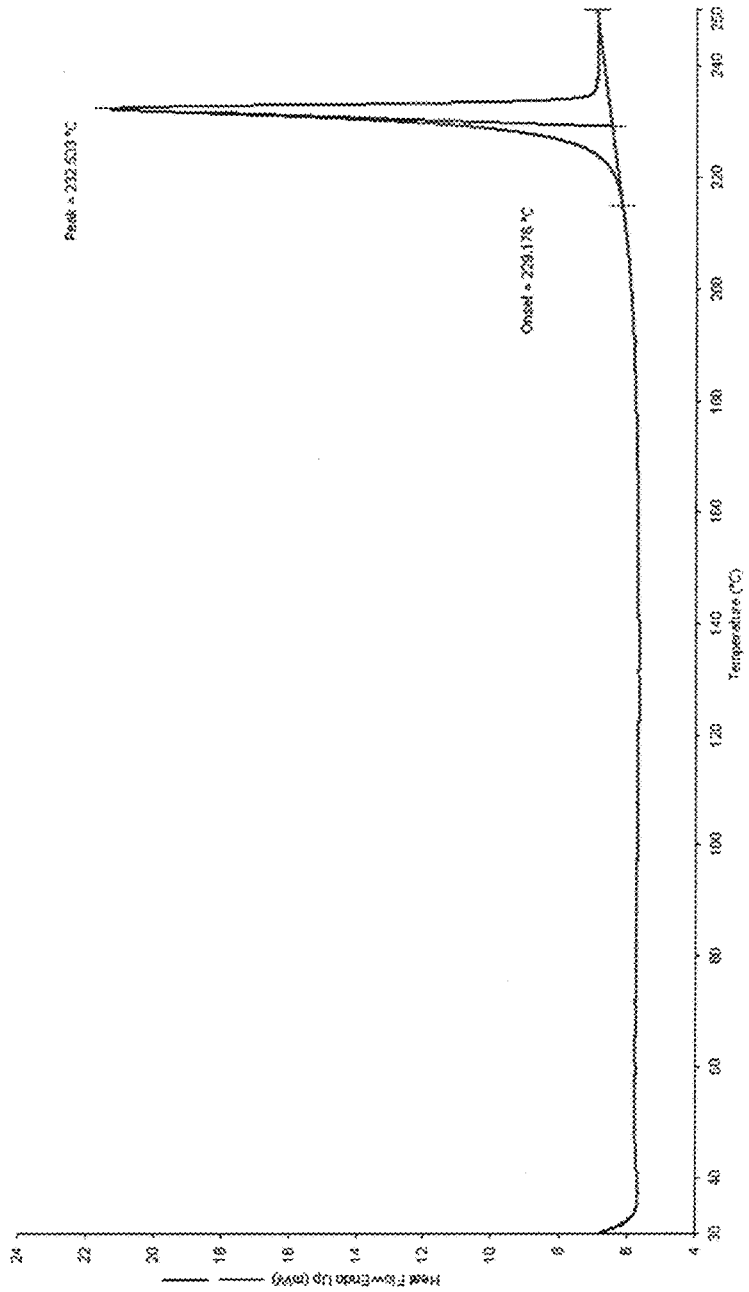
Figure 3 : DSC diagram of N-(2,6-diethylphenyl)-8-({4-[4-(dimethylamino)piperidin-1-yl]-2-methoxyphenyl}amino)-1-methyl-4,5-dihydro-1H-pyrazolo[4,3-h]quinazoline-3-carboxamide phosphate Form I

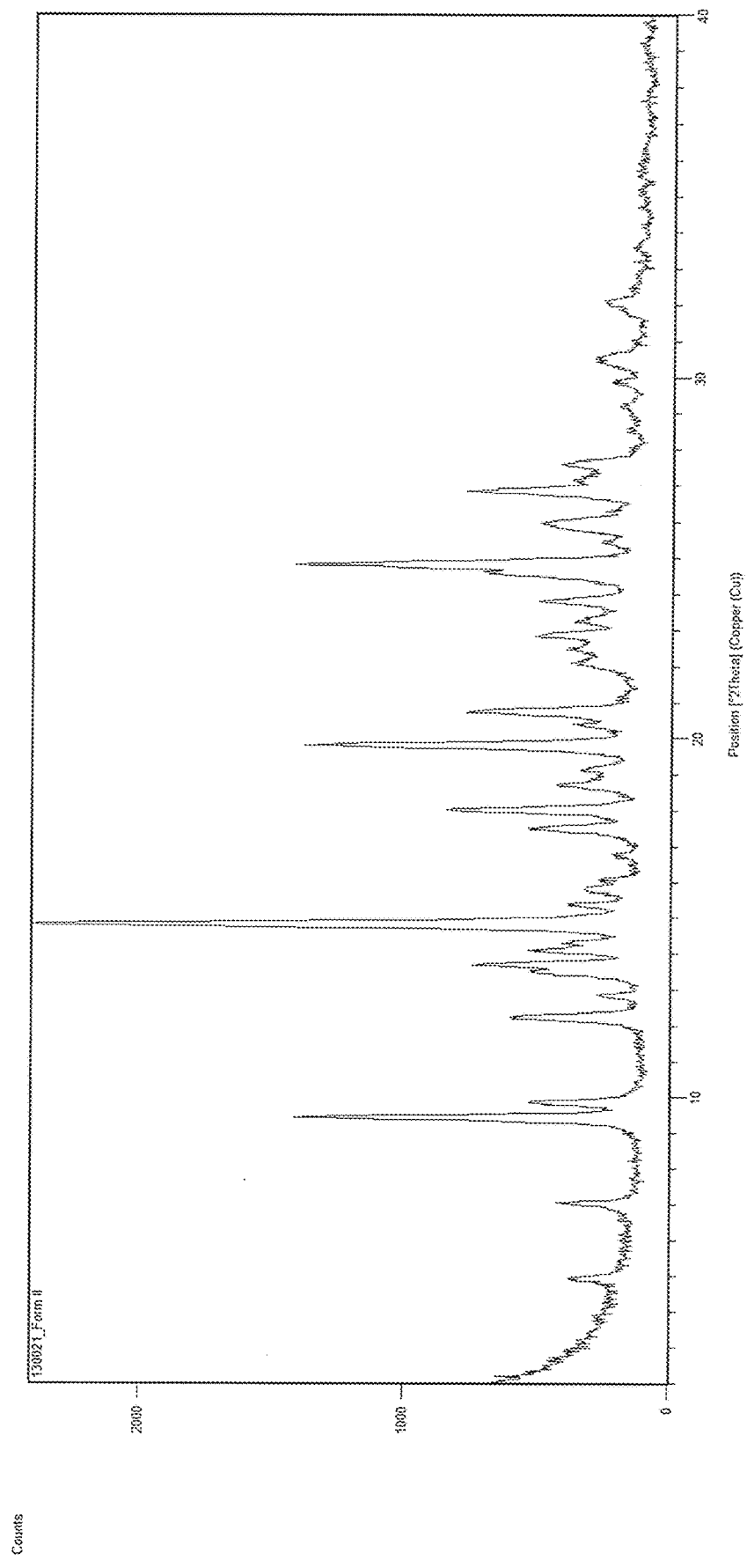
Figure 4: X-ray powder diffraction diagram of N-(2,6-diethylphenyl)-8-({4-[4-(dimethylamino)piperidin-1-yl]-2-methoxyphenyl}amino)-1-methyl-4,5-dihydro-1H-pyrazolo[4,3-h] quinazoline-3-carboxamide phosphate Form II

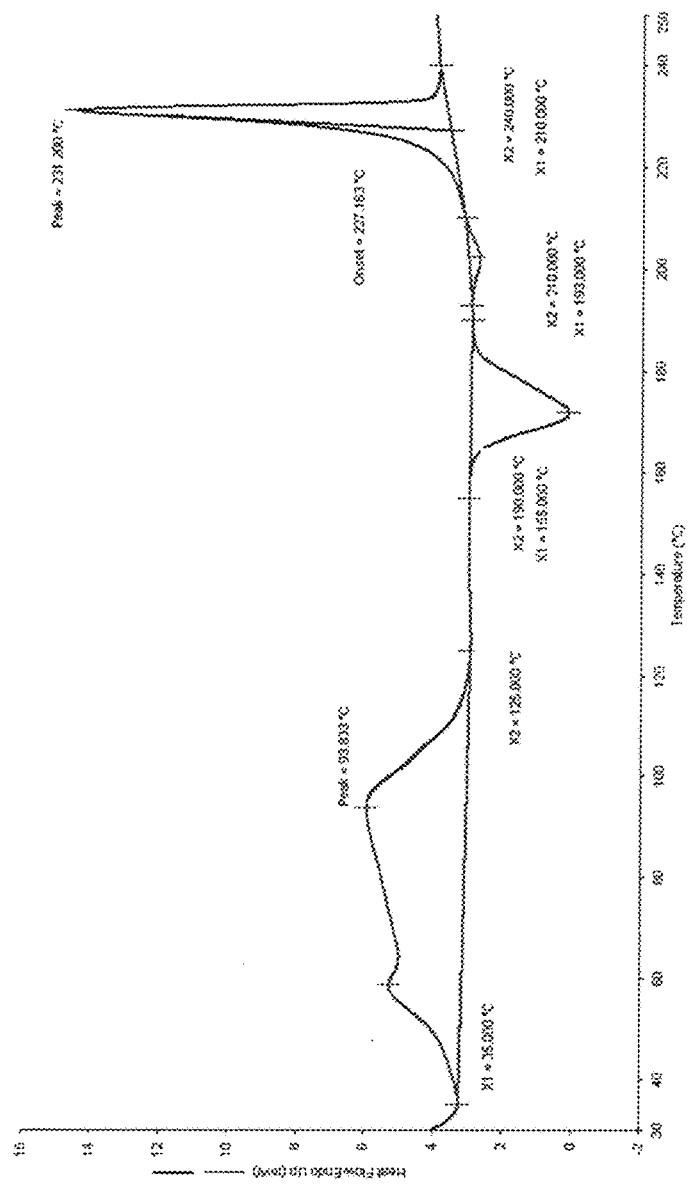
Figure 5: DSC diagram of N-(2,6-diethylphenyl)-8-({4-[4-(dimethylamino)piperidin-1-yl]-2-methoxyphenyl}amino)-1-methyl-4,5-dihydro-1H-pyrazolo[4,3-h]quinazoline-3-carboxamide phosphate Form II

SALT OF N-(2,6-DIETHYLPHENYL)-8-({4-[4-(DIMETHYLAMINO)PIPERIDIN-1-YL]-2-METHOXYPHENYL}AMINO)-1-METHYL-4,5-DIHYDRO-1H-PYRAZOLO[4,3-H]QUINAZOLINE-3-CARBOXAMIDE, ITS PREPARATION, AND FORMULATIONS CONTAINING IT

The present invention relates to a new salt of N-(2,6-diethylphenyl)-8-({4-[4-(dimethyl amino)piperidin-1-yl]-2-methoxyphenyl}amino)-1-methyl-4,5-dihydro-1H-pyrazolo[4,3-h]quinazoline-3-carboxamide of formula (I):

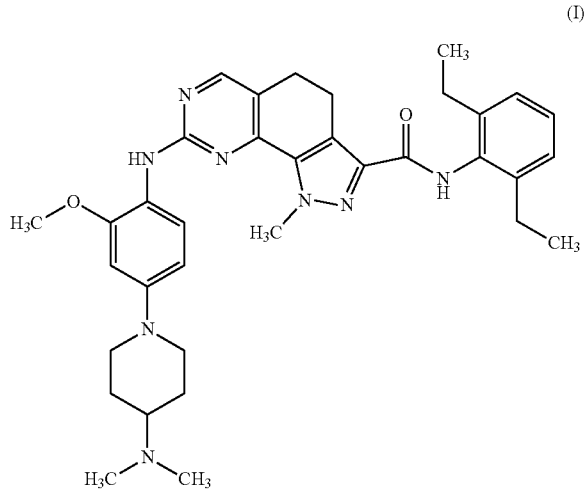 [SMILES: CCc1cccc(CC)c1NC(=O)c1nn(C)c2c1CCc1cnc(Nc3ccc(N4CCC(N(C)C)CC4)cc3OC)nc1-2]

(I)

to its preparation process and also to pharmaceutical compositions containing it.

N-(2,6-diethylphenyl)-8-({4-[4-(dimethylamino)piperidin-1-yl]-2-methoxyphenyl}amino)-1-methyl-4,5-dihydro-1H-pyrazolo[4,3-h]quinazoline-3-carboxamide has very valuable pharmacological properties in the field of oncology. It has in fact been shown that N-(2,6-diethylphenyl)-8-({4-[4-(dimethylamino)piperidin-1-yl]-2-methoxyphenyl}amino)-1-methyl-4,5-dihydro-1H-pyrazolo[4,3-h]quinazoline-3-carboxamide has the ability to inhibit MPS1 (Monopolar Spindle 1) kinase, also known as TTK (Tyrosine and Serine/Threonine kinase). This ability confers to the molecule therapeutic benefit in the treatment of several diverse cancers, cell proliferative disorders, viral infections, autoimmune and neurodegenerative disorders. Among the cancers envisaged for treatment there may be mentioned, without implying any limitation, carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma mesothelioma, highly aneuploid tumors and tumors which do overexpress mitotic checkpoint components like MPS1, MAD2, MAD1, BUB1, BUBR1, BUB3 and others.

Among the cell proliferative disorder envisaged for treatment there may be mentioned, without implying any limitation, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The preparation and therapeutic use of N-(2,6-diethylphenyl)-8-({4-[4-(dimethyl amino)piperidin-1-yl]-2-methoxyphenyl}amino)-1-methyl-4,5-dihydro-1H-pyrazolo[4,3-h]quinazoline-3-carboxamide have been described, for example, in the European patent specification EP2303891, the content of which is incorporated by reference.

In view of the pharmaceutical value of this compound it is important to be able to obtain the active compound in excellent yields, with high purity and with excellent reproducibility. Furthermore, taking into account the intravenous way of administration, it is also crucial to have very good solubility properties. It was rapidly found that the base described in the prior art presented problems of purification resulting in non-optimal purity, and presented also poor solubility. After numerous research studies, it was possible to identify a new salt combining various advantages, especially relating to purification, to reproducibility of the process for obtaining it and to yield, but also unexpectedly having the advantage of very significantly improving the solubility of the active compound. Furthermore, although much more water soluble, this new salt doesn't exhibit higher hygroscopicity than the free base. This new salt accordingly has all the qualities essential to its use as a medicament, from both the physicochemical and the pharmacokinetic point of view.

The present invention accordingly relates to a new salt of N-(2,6-diethylphenyl)-8-({4-[4-(dimethylamino)piperidin-1-yl]-2-methoxyphenyl}amino)-1-methyl-4,5-dihydro-1H-pyrazolo[4,3-h]quinazoline-3-carboxamide, more especially N-(2,6-diethylphenyl)-8-({4-[4-(dimethylamino)piperidin-1-yl]-2-methoxyphenyl}amino)-1-methyl-4,5-dihydro-1H-pyrazolo[4,3-h]quinazoline-3-carboxamide phosphate of formula (II):

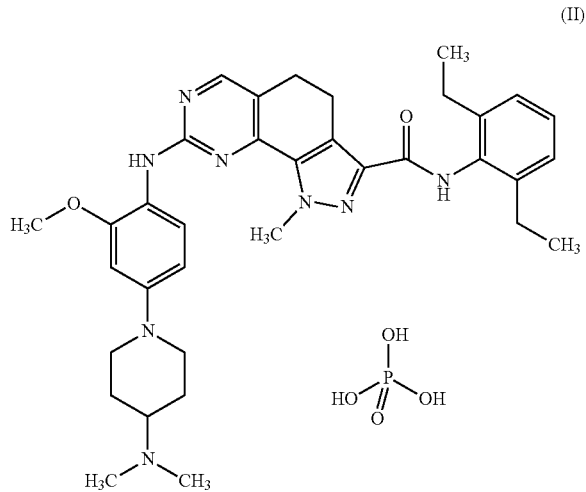 [SMILES: CCc1cccc(CC)c1NC(=O)c1nn(C)c2c1CCc1cnc(Nc3ccc(N4CCC(N(C)C)CC4)cc3OC)nc1-2 ; O=P(O)(O)O]

(II)

This new salt has the following advantages:
a simple and reproducible process for obtaining it with excellent yield;

a high chemical purity, and low hygroscopicity;
an increased solubility in both water and physiologic serum, making it of great interest for intravenous administration.

The invention relates also to a process for obtaining N-(2,6-diethylphenyl)-8-({4-[4-(dimethylamino)piperidin-1-yl]-2-methoxyphenyl}amino)-1-methyl-4,5-dihydro-1H-pyrazolo[4,3-h]quinazoline-3-carboxamide phosphate.

For example, it can be started from the starting material ethyl 8-[(4-bromo-2-methoxy phenyl)amino]-1-methyl-4,5-dihydro-1H-pyrazolo[4,3-h]quinazoline-3-carboxylate, as obtained in EP 2303891, which is reacted with 2,6-diethyl-aniline in presence of a strong base to give 8-[(4-bromo-2-methoxyphenyl)amino]-N-(2,6-diethylphenyl)-1-methyl-4,5-dihydro-1H-pyrazolo[4,3-h]quinazoline-3-carboxamide, which is then reacted with N,N-dimethylpiperidin-4-amine to yield compound of formula (I) that is then mixed with 1 to 2 equivalents of an $H_3PO_4$ solution to give N-(2,6-diethylphenyl)-8-({4-[4-(dimethylamino) piperidin-1-yl]-2-methoxyphenyl}amino)-1-methyl-4,5-dihydro-1H-pyrazolo[4,3-h]quinazoline-3-carboxamide phosphate of formula (II).

The compound of formula (II) according to the invention has a good stability over time under denaturing conditions (40° C./75% Relative Humidity (RH)):

| | $t_0$ | 1 month 40° C./75% RH Open bottle |
|---|---|---|
| Phosphate salt of formula (II) Chemical purity in % | 99.5 | 99.4 |

It has been established that the new salt of the invention had also improved solubility properties:
in preliminary test, in situ salt formation from the amorphous base at room temperature indicated that the phosphate salt had the capacity to improve solubility at least 25 times more than the hydrochloride salt and at least 24 000 times more than the free base:

| | target solution | Solubility | |
|---|---|---|---|
| Compound | concentration in water (mg/ml as free base) | 1 hour (mg/ml as free base) | 24 hours (mg/ml as free base) |
| Free Base | 10.0 | <0.001 | <0.001 |
| In situ HCl salt | 27.6 | 1.05 | 0.87 |
| In situ phosphate salt | 27.5 | >24.3 | >24.7 | further investigations with the crystalline form I of the phosphate salt of formula (II) indicated a solubility at room temperature of at least 130 mg/ml expressed as free base, both in water and in NaCl 0.9%:

| Compound | Medium | target solution concentration in water or NaCl (mg/ml as free base) | Solubility 1 hour (mg/ml as free base) | 24 hours (mg/ml as free base) |
|---|---|---|---|---|
| Free Base | water | 10.0 | <0.001 | <0.001 |
| Phosphate salt | water | 150.0 | 87.5 | 130.2 |
| Phosphate salt | NaCl 0.9% | 150.0 | 81.0 | 133.6 |

The phosphate salt was identified during the salt screening as improving significantly the solubility of the drug substance while having a low propensity to hygroscopicity as demonstrated by Dynamic Vapour Sorption analysis below:

| | Water uptake at 30% RH | Water uptake at 60% RH | Water uptake at 90% RH |
|---|---|---|---|
| Free base | 0.4 | 1 | 2.8 |
| Phosphate salt | 0.4 | 1.0 | 2.5 |

In an advantageous alternative, the last step of the process used to obtain compound of formula (II) can be performed in an organic solvent, and more specifically polar solvent such as for example THF (tetrahydrofurane), EtOH, MeOH, (1- or 2-) propanol, (1- or 2-) butanol, tertbutanol, 2-methoxyethanol, dioxane, ethyl acetate, isopropyl acetate, acetonitrile, acetone, MTBE (methyltertbutylether), MIBK (methylisobutylketone), DMSO (dimethylsulfoxide) and mixtures thereof.

In that case, the compound of formula (II) obtained is characterised by the polymorphic form named form I.

This new form I is characterized by the following Bragg's angles 2-theta (expressed in °±0.2) obtained from the X-ray powder diffractogram: 2.76, 8.10, 10.79, 13.49, 16.13, 17.37, 17.62, 19.77, 21.94, 24.18, 24.66.

In another advantageous alternative, the last step of the process used to obtain compound of formula (II) is performed in water leading to a new hydrated polymorphic form named form II.

This new form II is characterized by the following Bragg's angles 2-theta (expressed in °±0.2) obtained from the X-ray powder diffractogram: 9.43, 9.86, 12.23, 13.70, 14.81, 18.01, 19.78, 20.73, 24.55, 24.82, 26.81.

The invention relates also to pharmaceutical compositions comprising as active ingredient the compound of formula (II) according to the invention, together with one or more inert, non-toxic, appropriate excipients. Among the pharmaceutical compositions according to the invention there may be mentioned more especially those that are suitable for oral, parenteral (intravenous or subcutaneous) or nasal administration, tablets or dragées, granules, sublingual tablets, capsules, lozenges, suppositories, creams, ointments, dermal gels, injectable preparations, drinkable suspensions and chewing gums.

The pharmaceutical forms comprising the compound of formula (II) according to the invention, will be used in the treatment of cancers, cell proliferative disorders, viral infections, autoimmune and neurodegenerative disorders. Among the cancers envisaged for treatment there may be mentioned, without implying any limitation, carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma, mesothelioma, highly aneuploid tumors and tumors which do overexpress mitotic checkpoint components like MPS1, MAD2, MAD1, BUB1, BUBR1, BUB3 and others.

Among the cell proliferative disorder envisaged for treatment there may be mentioned, without implying any limitation, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The useful dosage can be varied according to the nature and severity of the disorder, the administration route and the age and weight of the patient. The dosage varies from 1 mg to 1 g per day, in terms of the free base equivalent, in one or more administrations.

BRIEF DESCRIPTION OF THE FIGURES

FIG. 1 describes the X-ray diffraction diagram of amorphous form of the free base N-(2,6-diethylphenyl)-8-({4-[4-(dimethylamino)piperidin-1-yl]-2-methoxyphenyl-2-methoxyphenyl}amino)-1-methyl-4,5-dihydro-1H-pyrazolo[4,3-h] quinazoline-3-carboxamide.

FIG. 2 describes the X-ray diffraction diagram of form I of the N-(2,6-diethylphenyl)-8-({4-[4-(dimethylamino)piperidin-1-yl]-2-methoxyphenyl}amino)-1-methyl-4,5-dihydro-1H-pyrazolo[4,3-h] quinazoline-3-carboxamide phosphate.

FIG. 3 describes the DSC diagram of form I of the N-(2,6-diethylphenyl)-8-({4-[4-(dimethylamino)piperidin-1-yl]-2-methoxyphenyl}amino)-1-methyl-4,5-dihydro-1H-pyrazolo[4,3-h] quinazoline-3-carboxamide phosphate.

FIG. 4 describes the X-ray diffraction diagram of form II of the N-(2,6-diethylphenyl)-8-({4-[4-(dimethylamino)piperidin-1-yl]-2-methoxyphenyl}amino)-1-methyl-4,5-dihydro-1H-pyrazolo[4,3-h] quinazoline-3-carboxamide phosphate.

FIG. 5 describes the DSC diagram of form II of the N-(2,6-diethylphenyl)-8-({4-[4-(dimethylamino)piperidin-1-yl]-2-methoxyphenyl}amino)-1-methyl-4,5-dihydro-1H-pyrazolo[4,3-h] quinazoline-3-carboxamide phosphate.

The Examples hereinbelow illustrate the invention but do not limit it in any way.

Example 1: N-(2,6-Diethylphenyl)-8-({4-[4-(Dimethylamino)Piperidin-1-Yl]-2-Methoxyphenyl}Amino)-1-Methyl-4,5-Dihydro-1H-Pyrazolo[4,3-H]Quinazoline-3-Carboxamide Phosphate, Form I

Step A: 8-([4-Bromo-2-methoxyphenyl}amino)-N-(2,6-diethylphenyl)-1-methyl-4,5-dihydro-1H-pyrazolo[4,3-h]quinazoline-3-carboxamide To a solution containing 2.32 kg of 8-[(4-bromo-2-methoxyphenyl)amino]-1-methyl-4,5-dihydro-1H-pyrazolo[4,3-h]quinazoline-3-carboxamide in 34.8 L of THF is added 0.877 L of 2,6-diethylaniline. 15.2 L of LiHMDS are then added dropwise at −10° C. Reaction is stirred 1.5 hour, and LiHMDS is added until completion. Then 30.17 L of a NaCl solution are added and the organic phase is washed twice with NaCl solution, and evaporated. A solution of water/acetone is then added to the residue, and the solution refluxed, then cooled at 5° C. The precipitate is then filtered to give the title product as a light yellow powder.

Melting point: 218-220° C.
MS calc.: 561.1608; MS found: 561.1591

Step B: N-(2,6-Diethylphenyl)-8-({4-[4-(dimethylamino)piperidin-1-yl]-2-methoxy phenyl}amino)-1-methyl-4,5-dihydro-1H-pyrazolo[4,3-h]quinazoline-3-carboxamide phosphate, Form 1

0.55 kg of 8-[(4-bromo-2-methoxyphenyl)amino]-N-(2,6-diethylphenyl)-1-methyl-4,5-dihydro-1H-pyrazolo[4,3-h] quinazoline-3-carboxamide obtained in step A are charged in a reactor with 6 L of THF. To the stirred mixture, 3.3 g of palladium acetate and 13.7 g of RuPhos in 3.9 L THF are added at room temperature under nitrogen.

0.15 kg of 4-dimethylamino-piperidine are added to the reaction mixture with 0.55 L of THF, the internal temperature is increased to 50° C. and 3.9 L of 1M LiHMDS in THF are dropped.

The reaction mixture is stirred at 50° C. for 4.5 hours and then cooled to room temperature. 12 L of water are added; phases are separated and the aqueous one is extracted once with 7 L of MTBE.

The organic phases are washed with brine and then extracted twice with 10% citric acid aqueous solution. The citric acid phases are pooled and added with a 2/1 mixture of MTBE/THF. The biphasic mixture is cooled to 10° C. and 35% aqueous NaOH is added until pH 9. The organic phase is separated and treated with SPM32 resin at reflux. The resin is filtered away washing with 2/1 mixture of MTBE/THF and the solvent is partially evaporated. Absolute Ethanol is added and evaporated; the procedure is repeated and then 12 L of absolute ethanol are added. The obtained solution is heated at 60° C. and a solution of 67 mL of 85% $H_3PO_4$ mixed with 0.6 L of absolute EtOH is added dropwise. A solution is kept until about half addition, and then a precipitate forms. The suspension is heated to reflux (78.0° C.) for 18 minutes and then cooled to 23° C. in 1 hour and 25 minutes. The suspension is further cooled to 5° C. in 1 hour and kept at 5° C. for 22.5 hours. The title compound is isolated by filtration; the wet cake is washed with 2.5 L of absolute EtOH and dried under vacuum at 50° C. till constant weight. The title compound is obtained in the form of a yellow powder.

Melting point 220-223° C. with decomposition.

Example 2: N-(2,6-Diethylphenyl)-8-({4-[4-(Dimethylamino)Piperidin-1-Yl]-2-Methoxyphenyl}Amino)-1-Methyl-4,5-Dihydro-1H-Pyrazolo[4,3-H]Quinazoline-3-Carboxamide Phosphate, Form I

Step A: N-(2,6-Diethylphenyl)-8-({4-[4-(dimethylamino)piperidin-1-yl]-2-methoxy phenyl}amino)-1-methyl-4,5-dihydro-1H-pyrazolo[4,3-h]quinazoline-3-carboxamide (free base)

A solution, containing 213 mg of Pd(OAc)$_2$ and 897 mg of RuPhos in 177 mL of THF, is added to 21.53 g of 8-[(4-bromo-2-methoxyphenyl)amino]-N-(2,6-diethylphenyl)-1-methyl-4,5-dihydro-1H-pyrazolo[4,3-h]quinazoline-3-carboxamide obtained I Step A of Example 1 in 250 mL of THF, at room temperature under nitrogen. The mixture is heated at 40° C. before sequential addition of 152 mL of LiHMDS 1M in THF and 10.7 mL of N,N-dimethylpiperidin-4-amine. The reaction is kept at 40° C. for 2.5 hours and then cooled to room temperature. 300 mL of brine are then added and the organic separated phase is washed with 200 mL of brine.

The organic phase is treated with 2.8 g of activated charcoal; the mixture is filtered on a dicalite pad, evaporated to dryness and purified by silica-gel chromatography eluting with DCM/EtOH/NH$_3$ 95:5:0.5. The pooled fractions are evaporated to residue, dissolved in EtOAc, washed five times with a saturated solution of sodium bicarbonate and with water, and then evaporated to dryness. The product is dried in oven at 50° C. for 7 hours, and at 40° C. for 64 hours. The free base is obtained as an amorphous yellow powder and characterized by its X-Ray diffraction diagram (see FIG. 1).

Step B: N-(2,6-Diethylphenyl)-8-({4-[4-(dimethyl-amino)piperidin-1-yl]-2-methoxy phenyl}amino)-1-methyl-4,5-dihydro-1H-pyrazolo[4,3-h] quinazoline-3-carboxamide phosphate, Form I 3.50 g of N-(2,6-diethylphenyl)-8-({4-[4-(dimethyl-amino)piperidin-1-yl]-2-methoxy phenyl}amino)-1-methyl-4,5-dihydro-1H-pyrazolo[4,3-h]quinazoline-3-carboxamide amorphous free base obtained in Step A, in 105 mL of absolute ethanol is heated to 60° C. under nitrogen. To this mixture a freshly prepared solution of 0.682 g of 85% phosphoric acid in 17.5 mL of ethanol was added dropwise over a period of 20 minutes under efficient stirring. The resulting suspension was heated to reflux (bath temperature 82-84° C.) for 5 minutes, then it was allowed to cool spontaneously to room temperature over a period of 2 hours and finally aged at +4° C. for 16 hours. The solid was isolated by filtration, washed with 17.5 mL of ethanol on the filter and dried at +50° C. under vacuum for 10 hours yielding the title compound in the form of a yellow powder.

Melting point 220-223° C. with decomposition.

The title product N-(2,6-diethylphenyl)-8-({4-[4-(dimethylamino)piperidin-1-yl]-2-methoxyphenyl}amino)-1-methyl-4,5-dihydro-1H-pyrazolo[4,3-h]quinazoline-3-carboxamide phosphate, Form I of Examples 1 and 2 is characterised by its X-ray powder diffraction diagram carried out using a Thermo/ARL XTRA apparatus, and shown in FIG. 2.

This instrument is based on Bragg-Brentano geometry and equipped with a Cu Kα generator working at 45 KV/40 mA (1.8 kW power) and a Peltier-cooled solid state detector. The spectral range was from 2 to 40° 2θ with a continuous scan acquisition at a rate of 1.20° 2θ/min. The samples were loaded on Silicon low background plates. The powder was flattened inside the holder by gently pressing with a microscope glass slide or other suitable tools.

The results are expressed in terms of interplanar distance d, Bragg's angle 2 theta (expressed in °±0.2) and relative intensity (expressed as a percentage relative to the most intense line):

| Pos. [°2Th.] | d-spacing [Å] | Rel. Int. [%] |
| --- | --- | --- |
| 2.76 | 31.96 | 100.00 |
| 8.10 | 10.90 | 37.71 |
| 10.79 | 8.19 | 27.69 |
| 13.49 | 6.56 | 35.45 |
| 14.70 | 6.02 | 17.98 |
| 14.79 | 5.98 | 12.17 |
| 15.26 | 5.80 | 15.02 |
| 15.47 | 5.72 | 15.26 |

-continued

| Pos. [°2Th.] | d-spacing [Å] | Rel. Int. [%] |
| --- | --- | --- |
| 15.75 | 5.62 | 11.11 |
| 16.13 | 5.49 | 57.81 |
| 16.45 | 5.38 | 15.80 |
| 17.37 | 5.10 | 22.52 |
| 17.62 | 5.03 | 34.76 |
| 17.80 | 4.98 | 27.97 |
| 18.17 | 4.88 | 13.67 |
| 19.77 | 4.49 | 20.09 |
| 20.35 | 4.36 | 13.56 |
| 21.94 | 4.05 | 24.02 |
| 22.25 | 3.99 | 10.35 |
| 23.61 | 3.77 | 19.98 |
| 23.94 | 3.71 | 16.75 |
| 24.18 | 3.68 | 26.62 |
| 24.41 | 3.64 | 15.16 |
| 24.66 | 3.61 | 25.6 |
| 25.00 | 3.56 | 16.06 |

Bragg's angles 2-theta (expressed in +0.2) characteristic of the X-ray powder diffraction diagram are as follows: 2.76, 8.10, 10.79, 13.49, 16.13, 17.37, 17.62, 19.77, 21.94, 24.18, 24.66.

The title compound of Examples 1 and 2 was also characterised by its DSC diagram, carried out with a Perkin-Elmer DSC-7, using 50 μL vented aluminum DSC pans loaded with about 2-4 mg of sample. An aluminum disc was placed over the powder obtaining a thin layer and improving thermal exchange. The reference was a void pan of the same kind. Indium, Tin and Lead (LGC certified reference materials) were used to assess the calibration of the apparatus with regard to the temperature scale and the enthalpy response. The samples were analyzed under nitrogen flow at a heating rate of 10° C./min. Onset and peak temperatures (° C.) were generally considered parameters of interest. The diagram obtained is shown in FIG. 3 with an onset of melting of 229° C.

Example 3: N-(2,6-Diethylphenyl)-8-({4-[4-(Dimethylamino)Piperidin-1-Yl]-2-Methoxyphenyl}Amino)-1-Methyl-4,5-Dihydro-1H-Pyrazolo[4,3-H]Quinazoline-3-Carboxamide Phosphate, Tetrahydrate, Form II 304 mg of compound obtained in Step A of Example 2 are loaded in a three necks round bottom flask of 25 mL and 12 mL of water are added at room temperature. The suspension that is obtained is stirred while heating at 61-62° C.; pH is about 5.3. After 1 hour stirring, 35.9 μL of H$_3$PO$_4$ are added plus 5 mL of water and almost instantaneously everything get into solution and the pH lowered to 3.1. The solution is heated to 70° C. for 1 h in order to ensure complete dissolution, pH=3.2. The heating bath is removed and the vessel is left to cool to room temperature then stirred for 2 hours. The vessel is cooled to 5° C. by leaving it in the refrigerator overnight leading to a yellow precipitate crashing out of the solution. The solid was left to settle within the mixture at room temperature and the supernatant solution was removed. The remaining solid was dried in oven at 50° C. under vacuum for 18 h. The compound of the title was obtained as a yellow solid.

Broad dehydration endotherm: 35-125° C.

Exotherm of crystallisation (T$_{offset}$): 190° C.

The title product is characterised by its powder diffraction diagram, carried out using a Thermo/ARL XTRA apparatus. This instrument is based on Bragg-Brentano geometry and equipped with a Cu Kα generator working at 45 KV/40 mA (1.8 kW power) and a Peltier-cooled solid state detector. The spectral range was from 2 to 40° 2θ with a continuous scan acquisition at a rate of 1.20° 2θ/min which makes it possible to identify the following crystal parameters:

unit cell parameters: a=13.866(2) Å; b=18.824(2) Å; c=7.2575(7) Å; alpha=92.014(8)°; beta=91.813(7)°; gamma=107.294(8)° space group: P-1 (2) (triclinic)

The title product was also characterised by its X-ray powder diffraction diagram shown in FIG. 4 carried out using a Thermo/ARL XTRA apparatus. This instrument is based on Bragg-Brentano geometry and equipped with a Cu Kα generator working at 45 KV/40 mA (1.8 kW power) and a Peltier-cooled solid state detector. The spectral range was from 2 to 400 2θ with a continuous scan acquisition at a rate of 1.20° 2θ/min. The samples were loaded on Silicon low background plates. The powder was flattened inside the holder by gently pressing with a microscope glass slide or other suitable tools.

The results are expressed in terms of interplanar distance d, Bragg's angle 2 theta (expressed in °±0.2) and relative intensity (expressed as a percentage relative to the most intense line):

| Pos. [°2Th.] | d-spacing [Å] | Rel. Int. [%] |
| --- | --- | --- |
| 7.03 | 12.57 | 11.00 |
| 9.43 | 9.37 | 56.04 |
| 9.86 | 8.97 | 19.21 |
| 12.23 | 7.23 | 22.55 |
| 13.47 | 6.57 | 17.30 |
| 13.70 | 6.46 | 27.62 |
| 14.08 | 6.29 | 17.19 |
| 14.23 | 6.19 | 12.02 |
| 14.81 | 5.98 | 100.00 |
| 15.36 | 5.77 | 11.17 |
| 17.49 | 5.07 | 17.11 |
| 18.01 | 4.92 | 30.83 |
| 18.70 | 4.74 | 12.02 |
| 19.78 | 4.48 | 52.48 |
| 20.73 | 4.28 | 26.92 |
| 22.85 | 3.89 | 15.52 |
| 23.80 | 3.74 | 13.98 |
| 24.55 | 3.62 | 21.43 |
| 24.82 | 3.58 | 53.06 |
| 25.91 | 3.44 | 15.20 |
| 26.81 | 3.32 | 25.51 |
| 27.16 | 3.28 | 10.01 |
| 27.56 | 3.23 | 12.10 |

Bragg's angles 2-theta (expressed in °±0.2) characteristic of the X-ray powder diffraction diagram: 9.43, 9.86, 12.23, 13.70, 14.81, 18.01, 19.78, 20.73, 24.55, 24.82, 26.81.

The compound of Example 3 was also characterised by its DSC diagram, carried out with a Perkin-Elmer DSC-7, using 50 μL vented aluminum DSC pans loaded with about 2-4 mg of sample. An aluminum disc was placed over the powder obtaining a thin layer and improving thermal exchange. The reference was a void pan of the same kind. Indium, Tin and Lead (LGC certified reference materials) were used to assess the calibration of the apparatus with regard to the temperature scale and the enthalpy response. The samples were analyzed under nitrogen flow at a heating rate of 10° C./min. Onset and peak temperatures (° C.) were generally considered parameters of interest.

The diagram obtained is shown in FIG. 5.

Example 4: Purity and Stability of N-(2,6-Diethylphenyl)-8-({4-[4-(Dimethylamino) Piperidin-1-Yl]-2-Methoxyphenyl}Amino)-1-Methyl-4,5-Dihydro-1H-Pyrazolo[4,3-H]Quinazoline-3-Carboxamide Phosphate Form I Under Long Term Conditions Purity and stability of N-(2,6-diethylphenyl)-8-({4-[4-(dimethylamino) piperidin-1-yl]-2-methoxyphenyl}amino)-1-methyl-4,5-dihydro-1H-pyrazolo[4,3-h]quinazoline-3-carboxamide phosphate Form I have been tested under long term conditions as follows:

| Test | Appearance | Total amount of impurities (%) | Drug substance (%) | Crystalline Form (XRD assessment) |
| --- | --- | --- | --- | --- |
| t₀ | Yellow powder | 0.06 | 99.94 | Form I |
| 1 month 5° C. | Yellow powder | 0.06 | 99.94 | Not tested |
| 1 month 25° C./60% RH | Yellow powder | 0.07 | 99.93 | Not tested |
| 3 months 5° C. | Yellow powder | 0.07 | 99.93 | Not tested |
| 3 months 25° C./60% RH | Yellow powder | 0.07 | 99.93 | Not tested |
| 9 months 5° C. | Yellow powder | 0.07 | 99.93 | Not tested |
| 12 months 5° C. | Yellow powder | 0.06 | 99.94 | Form I |
| 24 months 5° C. | Yellow powder | 0.09 | 99.91 | Form I |

Results show that N-(2,6-diethylphenyl)-8-({4-[4-(dimethylamino)piperidin-1-yl]-2-methoxyphenyl}amino)-1-methyl-4,5-dihydro-1H-pyrazolo[4,3-h]quinazoline-3-carboxamide phosphate Form I is stable at least up to 24 months.

Example 5: Solubility of N-(2,6-Diethylphenyl)-8-({4-[4-(Dimethylamino) Piperidin-1-Yl]-2-Methoxyphenyl}Amino)-1-Methyl-4,5-Dihydro-1H-Pyrazolo[4,3-H]Quinazoline-3-Carboxamide Phosphate Form I Testing conditions: about 730 mg of testing compound were suspended in 4 ml of WFI (water for injection) or Saline (0.9% NaCl) to test a target solubility of 150 mg/ml as free base. The suspensions were magnetically stirred for 24 hours at room temperature and protected from light in amber glass vial. Testing compound concentrations were determined after 1 and 24 hours.

All the withdrawn suspension/solution amounts were centrifuged and the superior solutions were analysed by HPLC after filtration and dilution.

The obtained results are summarized in the following table:

| Compound | Medium | target solution concentration in water or NaCl (mg/ml as free base) | Solubility 1 hour (mg/ml as free base) | Solubility 24 hours (mg/ml as free base) |
| --- | --- | --- | --- | --- |
| Free Base | water | 10.0 | <0.001 | <0.001 |
| Phosphate salt | water | 150.0 | 87.5 | 130.2 |
| Phosphate salt | NaCl 0.9% | 150.0 | 81.0 | 133.6 |

Example 6: Hygroscopicity Measurement of N-(2, 6-Diethylphenyl)-8-({4-[4-(Dimethylamino)Piperidin-1-Yl]-2-Methoxy Phenyl}Amino)-1-Methyl-4,5-Dihydro-1H-Pyrazolo[4,3-H]Quinazoline-3-Carboxamide Phosphate, Form I The compound to be tested is submitted to hygroscopicity test by means of a Dynamic Vapour Sorption apparatus (DVS 1000—Surface Measurement Systems).

The apparatus is briefly defined as a "controlled atmosphere microbalance" where the weighed sample is exposed to variations of the relative humidity (RH) at a constant and controlled temperature. An exactly weighed amount of the product (generally 5-10 mg) was analysed.

Results are reported in the following Table:

|  | Water uptake at 30% RH | Water uptake at 60% RH | Water uptake at 90% RH |
| --- | --- | --- | --- |
| Free base | 0.4 | 1 | 2.8 |
| Phosphate salt | 0.4 | 1.0 | 2.5 |

EXAMPLE 7: PHARMACEUTICAL COMPOSITIONS

A. Tablets

| 1000 tablets each containing a dose of 35 mg of Example 1 | 100 g |
| --- | --- |
| Wheat starch | 20 g |
| Maize starch | 20 g |
| Lactose | 30 g |
| Magnesium stearate | 2 g |
| Silica | 1 g |
| Hydroxypropylcellulose | 2 g |

B. Vials Lyophilisates

A bulk solution containing compound of Example 1, mannitol and Tween 80 is prepared, then lyophilized to obtain vials containing each 35 mg of compound of Example 1, 300 mg of mannitol and 5 mg of Tween 80.

Lyophilisate is re-suspended in 10 ml of water for injection.

The invention claimed is:

1. N-(2,6-diethylphenyl)-8-({4-[4-(dimethylamino)piperidin-1-yl]-2-methoxyphenyl} amino)-1-methyl-4,5-dihydro-1H-pyrazolo[4,3-h]quinazoline-3-carboxamide phosphate of formula (II):

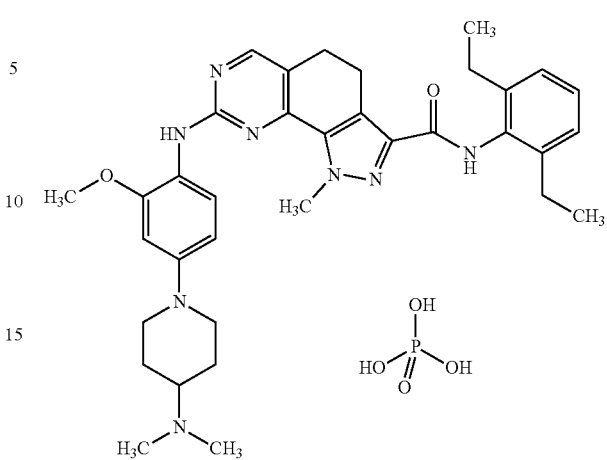

in the form of crystalline Form I having an X-ray powder diffractogram which exhibits the Bragg's angles 2 theta (expressed in terms of °±0.2) 2.76, 8.10, 10.79, 13.49, 16.13, 17.37, 17.62, 19.77, 21.94, 24.18 and 24.66.

2. A process for obtaining the crystalline Form I of the compound of formula (II) according to claim 1, which process comprises reacting the starting material N-(2,6-diethylphenyl)-8-({4-[4-(dimethylamino)piperidin-1-yl]-2-methoxyphenyl}amino)-1-methyl-4,5-dihydro-1H-pyrazolo[4,3-h]quinazoline-3- carboxamide, with 1 to 2 equivalents of a $H_3PO_4$ solution in ethanol.

3. N-(2,6-diethylphenyl)-8-({4- [4-(dimethylamino)piperidin-1-yl]-2-methoxyphenyl} amino)-1-methyl-4,5-dihydro-1H- pyrazolo[4,3-h]quinazoline-3-carboxamide phosphate of formula (II):

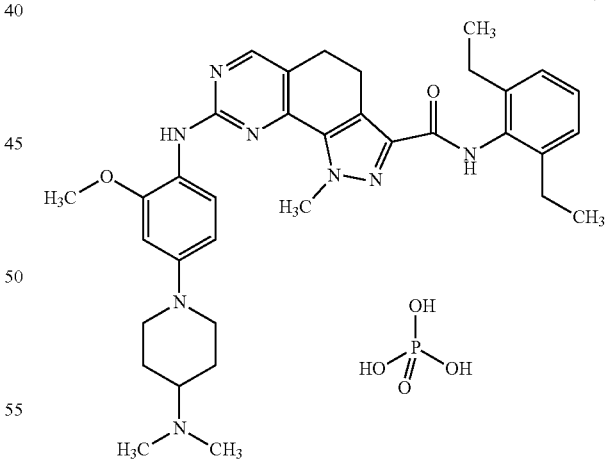

in the form of crystalline Form II having an X-ray powder diffractogram which exhibits the Bragg's angles 2 theta (expressed in terms of °±0.2) 9.43, 9.86, 12.23, 13.70, 14.81, 18.01, 19.78, 20.73, 24.55, 24.82 and 26.81.

4. A process for obtaining the crystalline Form II of the compound of formula (II) according to claim 3, which process comprises reacting the starting material N-(2,6-diethylphenyl)-8-({4-[4-(dimethylamino)piperidin-1- yl]-2-methoxyphenyl}amino)-1-methyl-4,5-dihydro-1H-pyrazolo

[4,3-h]quinazoline-3- carboxamide, with 1 to 2 equivalents of a $H_3PO_4$ solution in water.

5. A pharmaceutical composition comprising the crystalline Form I of the compound of formula (II) according to claim 1 in combination with one or more pharmaceutically acceptable excipients.

6. A pharmaceutical composition comprising the crystalline Form II of the compound of formula (II) according to claim 3 in combination with one or more pharmaceutically acceptable excipients.

* * * * *